US00PP21699P2

(12) United States Plant Patent
Jordan

(10) Patent No.: US PP21,699 P2
(45) Date of Patent: Feb. 8, 2011

(54) ARTICHOKE PLANT 'X42'

(50) Latin Name: *Cynara scolymus L.*
Varietal Denomination: X42

(75) Inventor: Stephen Jordan, Lompoc, CA (US)

(73) Assignee: Baroda Farms, Inc., Lompoc, CA (US)

( * ) Notice: Subject to any disclaimer, the term of this patent is extended or adjusted under 35 U.S.C. 154(b) by 0 days.

(21) Appl. No.: 12/587,834

(22) Filed: Oct. 13, 2009

(51) Int. Cl.
*A01H 5/00* (2006.01)

(52) U.S. Cl. ..... Plt./258

(58) Field of Classification Search ..... Plt./258
See application file for complete search history.

(56) References Cited

U.S. PATENT DOCUMENTS

PP15,807 P3 6/2005 Chahbandar

*Primary Examiner*—Annette H Para
(74) *Attorney, Agent, or Firm*—Townsend and Townsend and Crew LLP

(57) ABSTRACT

A new and distinct cultivar of *Cynara* named 'X42' that has improved productivity and year round harvest. 'X42' produces one central and about fifteen lateral edible immature flower buds, and four side shoots during the first year.

2 Drawing Sheets

Genus and species: The cultivar of this invention is botanically identified as *Cynara scolymus L.*

Variety denomination: The variety denomination is 'X42'.

BACKGROUND OF THE INVENTION

The present invention relates to a new and distinct cultivar of globe artichoke, a perennial herb that is grown as a food crop for the production of edible vegetable delicacies. The new invention is known botanically as *Cynara scolymus* and will be referred to hereinafter by the cultivar name 'X42'. *Cynara scolymus* is in the family Asteraceae, formerly known as Compositae.

An individual plant of *Cynara scolymus* 'X42' is comprised of main stem, lateral stems, leaves, and immature flower buds known as involucra. Each involucrum is made up of several series of phyllaries also known as involucral bracts. The edible parts of freshly harvested immature flower buds are the fleshy part of the bracts, the fleshy receptacle, and the uppermost part of the peduncle. If not harvested, but permitted to mature, flower buds will develop into flower heads known as capitula.

The new *Cynara* variety named 'X42' was discovered in October 2004 by the inventor as a natural somaclonal variant derived from the parent, an individual *Cynara scolymus* 'BCL 9-11' (U.S. Plant Pat. No. 15,807). The inventor selected 'X42' based on the criterion of high productivity of edible immature flower buds. 'X42' was discovered in and amongst a commercial crop of *Cynara scolymus* 'BCL 9-11' in Lompoc, Calif. At the time of discovery 'X42' was selected as a single plant and segregated and labeled for observation. No chemicals, nor other methods, known to the inventor, were used to induce the new variety 'X42'.

The first asexual propagation of 'X42' was conducted by the inventor in March 2005 using the method of crown divisions. Crown divisions then served as explant material for subsequent asexual propagation by tissue culture in June 2005. Under the inventor's supervision asexual propagation was conducted in Lompoc, Calif. where the plants were labeled and segregated. Since March 2005 under careful observation 'X42' has been determined uniform, stable and true to type in subsequent generations of asexual propagation.

BRIEF SUMMARY OF THE INVENTION

The closest comparison plant is *Cynara scolymus* 'BCL 9-11'. The comparison plant 'BCL 9-11' produces 1 central artichoke, 2.6 lateral artichokes and 3-4 side shoots the first year. The new *Cynara* variety named 'X42' is distinguishable from the comparison plant by increased productivity. 'X42' produces an increased quantity of lateral immature flower buds per plant.

The new *Cynara* variety named 'X42' is characterized by compact habit, yellow-green ribbed stems, yellow-green leaves, and high productivity, producing one central immature flower bud and 4.3 lateral immature flower buds that are uniform in shape, flavor, and tender consistency. Flower buds are yellow-green in color. The edible immature flower buds of 'X42' are harvested year round, with greatest productivity during the warmer months from March through September. Cultural requirements include full sun, well-draining soil, and moderate water. Hardiness is classified as USDA Zone 6.

The following traits have been repeatedly observed and represent the distinguishing characteristics of the new *Cynara* cultivar named 'X42'. 'X42' has greatest productivity during the warmer months from March through September. 'X42' exhibits high productivity, producing 1 central and 4.3 lateral immature flower buds as well as 3-5 side shoots during the first year. Each side shoot of 'X42' produces 1 central and 4.3 lateral immature flower buds per shoot. These traits in combination distinguish 'X42' from all other existing varieties of *Cynara* known to the inventor. 'X42' has not been tested under all possible conditions and phenotypic differences may be observed with variations in environmental, climatic, and cultural conditions, however, without any variance in genotype.

BRIEF DESCRIPTION OF THE DRAWINGS

The accompanying color photographs illustrate the overall appearance of the new *Cynara* cultivar named 'X42' showing color as true as is reasonably possible to obtain in color reproductions of this type. Photographs were taken using conventional techniques and although flower and foliage color may appear different from actual color due to light reflectance, they are as accurate as possible by conventional photography. Color in the photographs may differ from color values cited in the detailed botanical description, which accurately describe the actual color of the new variety 'X42'. Photographs were taken outdoors in indirect sunlight. Photographs were taken in April 2009 of 10-month-old field grown plants in Lompoc, Calif. Lompoc, Calif. is located on the central coast in Santa Barbara County. Conditions in Lompoc vary with air temperatures ranging from 15.5° C. to 26.6° C. The relative humidity is generally high. Prevailing winds are northwesterly and rainfall averages twelve inches per year.

BOTANICAL DESCRIPTION OF THE PLANT

Figure 1:
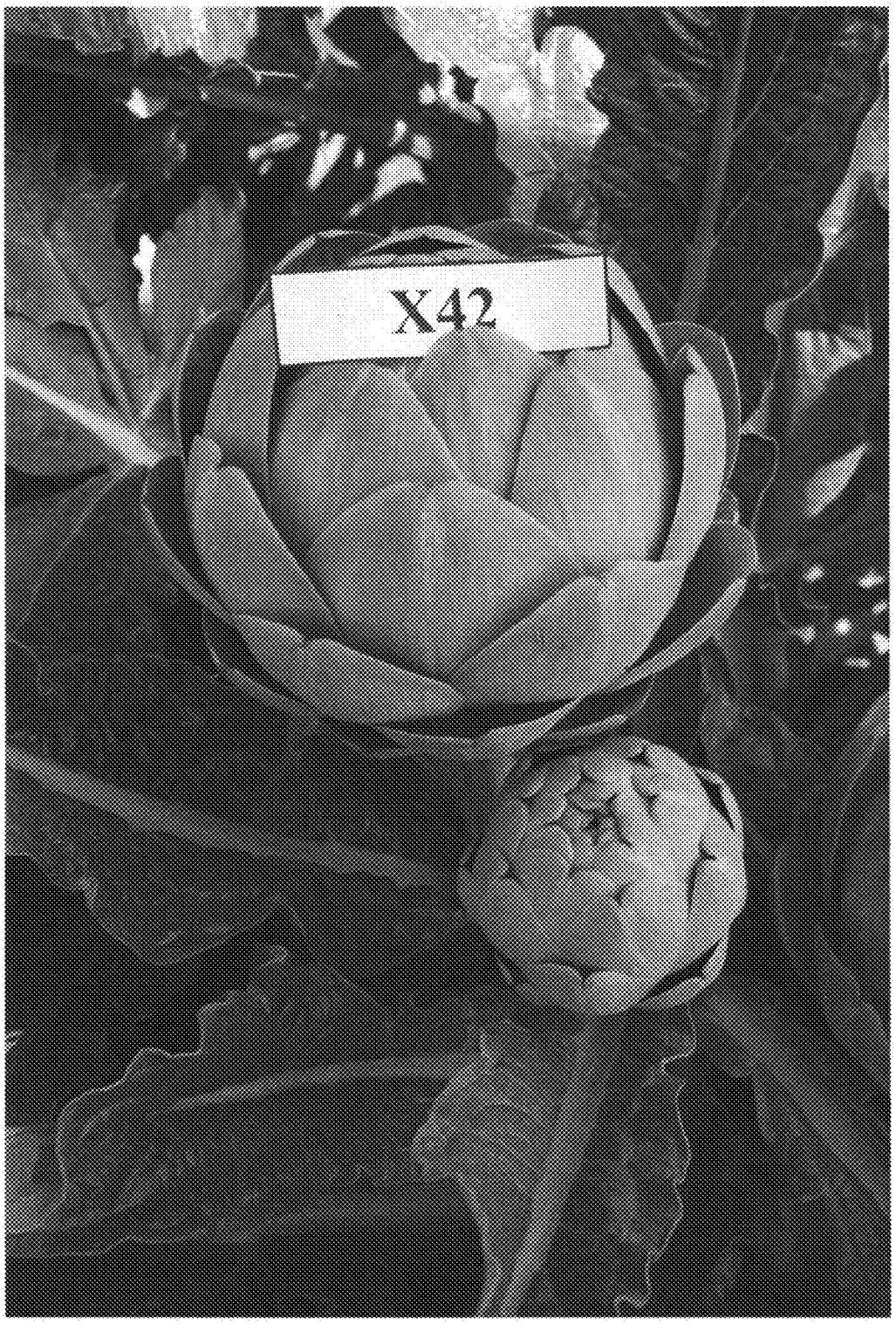
FIG. 1 depicts the central immature flower bud of 'X42'.
Figure 2:
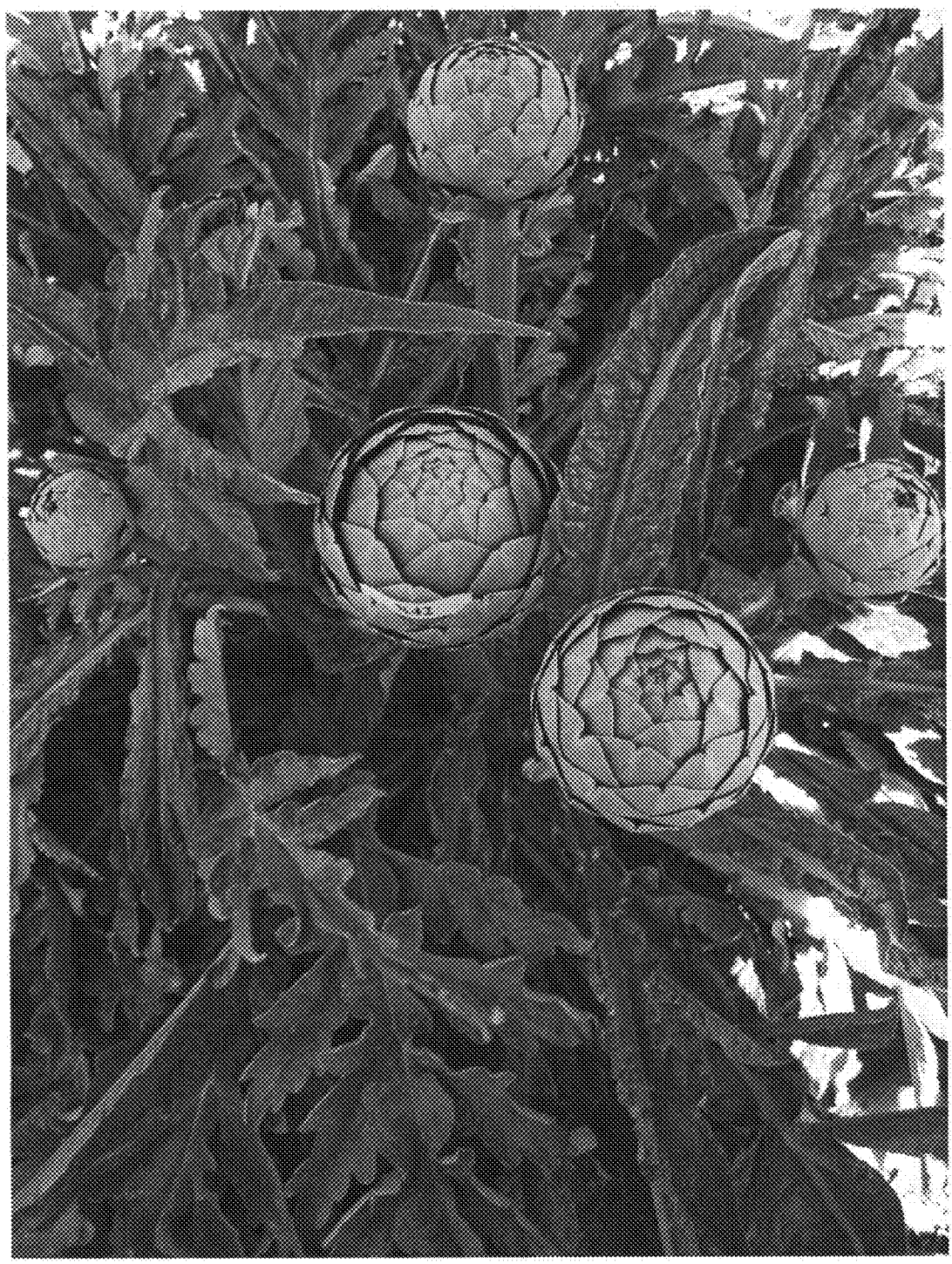
FIG. 2 depicts the lateral immature flower buds of 'X42'.

The following is a detailed botanical description of the new *Cynara* cultivar named 'X42'. Color determinations are in accordance with The 2001 Royal Horticultural Society Colour Chart of London, England, except where general color terms of ordinary dictionary significance are used. The following observations, measurements and values describe 'X42' as grown in Lompoc, Calif. under conditions used in horticultural practice. The plants were grown in rows where row spacing (bed centers) was at 3 meters and individual plant spacing at 120 cm. Data were collected in April 2009 from 10-month-old field grown plants. Growing requirements are similar to the requirements for other *Cynara*.

General characteristics:

*Months of harvest.*—Year round with greatest productivity March through September.
*Habit.*—Compact.
*Vigor.*—Vigorous.
*Type.*—Perennial herb.
*Height at time of harvest.*—89 cm.
*Width at time of harvest.*—158 cm.
*Root system.*—Thick and fibrous.
*Hardiness.*—USDA Zone 6.
*Propagation method.*—Tissue culture and division.
*Crop time* (*range*).—5-6 months to produce a harvestable crop of edible immature flower buds.
*Disease resistance.*—None known to the inventor.
*Pest and disease susceptibility.*—Aphids, slugs, and leaf spot.
*Cultural requirements.*—Grow in full sun and well-draining soil, with moderate water.

Stem:

*Branching habit* (*range*).—Basal to caulescent.
*Length* (*average*).—50 cm.
*Diameter* (*range*).—5-7 cm.
*Surface.*—A combination of ribbed and tomentose.
*Shape.*—Columnar.
*Strength.*—Rigid.
*Color.*—146D (145B-146C).
*Side shoots* (*range*).—3-5 during first year.
*Internode* (*average*).—7 cm.

Foliage:

*Type.*—Evergreen.
*Arrangement.*—Spiral.
*Division.*—Simple.
*Margin* (*range*).—Laciniate to incised.
*Quantity* (*average*).—30 leaves per individual plant.
*Shape.*—Pinnatifid.
*Attachment.*—Decurrent.
*Leaf color* (*abaxial surface*).—147B (147C-148D).
*Leaf color* (*adaxial surface*).—147A (147B-148C).
*Length* (*range*).—40-90 cm.
*Width* (*range*).—10-42 cm.
*Apex* (*range*).—Acute to cuspidate.
*Base.*—Truncate.
*Lobe quantity* (*average*).—10 lobes per leaf.
*Lobe apex.*—Acute.
*Lobe length* (*average*).—20 cm.
*Lobe width* (*average*).—7.50 cm.
*Venation pattern.*—Reticulate.
*Vein color* (*abaxial surface*).—147A (147C-148D).
*Vein color* (*adaxial surface*).—157D (157D-157A).
*Surface* (*abaxial*).—Tomentose.
*Surface* (*adaxial*).—Pubescent.
*Appearance* (*abaxial surface*).—Dull.
*Appearance* (*adaxial surface*).—Semi-glossy.
*Stipules.*—None observed.
*Fragrance.*—None observed.
*Angle of leaf to stem* (*average*).—45°.

Involucrum (immature flower bud):

*Shape.*—Oblate.
*Apex.*—Flattened obtuse.
*Base.*—Truncate.
*Bud depth* (*range*).—8-12 cm.
*Bud diameter* (*range*).—12-16 cm.
*Form.*—Compact.
*Texture.*—Firm.
*Surface.*—Glabrous.
*Quantity* (*average*).—1 central and 4.3 lateral.
*Phyllary* (*involucral bract*).—Arrangement: Imbricate. Outer bract quantity (average): 50 per involucrum. Inner bract quantity (average): 50 per involucrum. Outer and inner bract shape (range): Ovate to rotund. Margin: Entire. Outer bract texture: Fleshy. Inner bract texture: Papyraceous. Height (average): 6.50 cm. Width (average): 5.25 cm. Bract surface (abaxial): Glabrous. Bract surface (adaxial): Glabrous. Outer bract color (abaxial surface): 147D (146D-147C). Outer bract color (adaxial surface): 147D (146D-147C). Inner bract color (abaxial surface): 155D (155D-155A). Inner bract color (adaxial surface): 155D (155D-155A). Outer bract appearance: Matte. Inner bract appearance: Irridescent. Apex: Spinescent. Base: Truncate. Spine color: 162C (162D-162A). Spine dimensions: 2 mm. in height and 1.50 mm. in width.
*Receptacle shape.*—Concavo-convex.
*Receptacle diameter* (*average*).—8 cm.
*Receptacle depth* (*average*).—2 cm.
*Receptacle color.*—159C (159D-159A).
*Receptacle texture.*—Firm.
*Bristle color.*—159D (159D-159A).
*Bristle quantity.*—500+.
*Bristle shape.*—Filamentous.
*Bristle length* (*average*).—1 cm.
*Bristle width* (*average*).—<1 mm.
*Bristle texture.*—Sericeous.
*Peduncle shape.*—Columnar.
*Peduncle length* (*average*).—16 cm.
*Peduncle diameter* (*average*).—2.40 cm.
*Peduncle color.*—146D (145B-146C).

*Peduncle strength.*—Rigid.

*Peduncle surface.*—A combination of ribbed and tomentose.

*Duration of cold storage* (*range*).—22-24 days.

*Cold storage temperature* (*range*).—1° to 2° Centigrade.

*Cold storage response.*—Negligible browning and softening at stem cut.

*Shelf life* (*range*).—22-28 days under mist.

*Weight* (*average*).—548.20 grams.

Mature inflorescence: None observed to date.

Reproductive organs: None observed to date.

Seed: None observed to date.

What is claimed is:

1. A new and distinct variety of artichoke plant having the characteristics substantially as described and illustrated herein.

* * * * *